(12) United States Patent
McCabe

(10) Patent No.: US 8,460,495 B2
(45) Date of Patent: Jun. 11, 2013

(54) METHOD FOR PRODUCING ABSORBENT ARTICLE WITH STRETCH FILM SIDE PANEL AND APPLICATION OF INTERMITTENT DISCRETE COMPONENTS OF AN ABSORBENT ARTICLE

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 354 days.

(21) Appl. No.: 12/979,154

(22) Filed: Dec. 27, 2010

(65) Prior Publication Data

US 2011/0155305 A1    Jun. 30, 2011

Related U.S. Application Data

(60) Provisional application No. 61/335,018, filed on Dec. 30, 2009.

(51) Int. Cl.
*A61F 13/15* (2006.01)
(52) U.S. Cl.
USPC ........... 156/164; 156/204; 156/226; 156/248; 156/267; 156/270
(58) Field of Classification Search
None
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,431,315 A | 10/1922 | Le Moine | |
| 1,605,842 A | 11/1926 | Jones | |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |

(Continued)

FOREIGN PATENT DOCUMENTS

| BE | 1007854 | 11/1995 |
|---|---|---|
| CA | 1146129 | 5/1983 |

(Continued)

OTHER PUBLICATIONS

USPTO Office Action dated Jun. 25, 2010 regarding U.S. Appl. No. 12/383,655, 24 pages.

(Continued)

*Primary Examiner* — Barbara J Musser
(74) *Attorney, Agent, or Firm* — Ryan Kromholz & Manion, S.C.

(57) ABSTRACT

Apparatus and methods are provided to allow for creation of a configured laminate of a non-woven material, to which a character strip is applied, the character strip exposed by either heat severing and removal of overlying materials, or intermittent application of overlying materials to leave the desired portions of the character strip exposed. A simultaneously formed core insert is applied to a preformed chassis web.

4 Claims, 11 Drawing Sheets

U.S. PATENT DOCUMENTS

| | | |
|---|---|---|
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,336,847 A | 8/1967 | Durat |
| 3,342,184 A | 9/1967 | Joa |
| 3,356,092 A | 12/1967 | Joa |
| 3,360,103 A | 12/1967 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Geller et al. |
| 3,903,768 A | 9/1975 | Amberg et al. |
| 3,904,147 A | 9/1975 | Taitel et al. |
| 3,918,968 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |

| | | | | | | |
|---|---|---|---|---|---|---|
| 4,634,482 A | 1/1987 | Lammers | | 5,226,992 A | 7/1993 | Morman |
| 4,641,381 A | 2/1987 | Heran et al. | | 5,246,433 A | 9/1993 | Hasse et al. |
| 4,642,150 A | 2/1987 | Stemmler | | 5,252,228 A | 10/1993 | Stokes |
| 4,642,839 A | 2/1987 | Urban | | 5,267,933 A | 12/1993 | Precoma |
| 4,650,530 A | 3/1987 | Mahoney et al. | | 5,273,228 A | 12/1993 | Yoshida |
| 4,663,220 A | 5/1987 | Wisneski et al. | | 5,275,676 A | 1/1994 | Rooyakkers et al. |
| 4,672,705 A | 6/1987 | Bors et al. | | 5,308,345 A | 5/1994 | Herrin |
| 4,675,016 A | 6/1987 | Meuli et al. | | 5,328,438 A | 7/1994 | Crowley |
| 4,675,062 A | 6/1987 | Instance | | 5,340,424 A | 8/1994 | Matsushita |
| 4,675,068 A | 6/1987 | Lundmark | | 5,368,893 A | 11/1994 | Sommer et al. |
| 4,686,136 A | 8/1987 | Homonoff et al. | | 5,389,173 A | 2/1995 | Merkatoris et al. |
| 4,693,056 A | 9/1987 | Raszewski | | 5,393,360 A | 2/1995 | Bridges et al. |
| 4,701,239 A | 10/1987 | Craig | | 5,407,507 A | 4/1995 | Ball |
| 4,720,415 A | 1/1988 | Vander Vielen et al. | | 5,407,513 A | 4/1995 | Hayden et al. |
| 4,723,698 A | 2/1988 | Schoonderbeek | | 5,415,649 A | 5/1995 | Watanabe et al. |
| 4,726,874 A | 2/1988 | Van Vliet | | 5,421,924 A | 6/1995 | Ziegelhoffer et al. |
| 4,726,876 A | 2/1988 | Tomsovic, Jr. | | 5,424,025 A | 6/1995 | Hanschen et al. |
| 4,743,241 A | 5/1988 | Igaue et al. | | 5,429,576 A | 7/1995 | Doderer-Winkler |
| 4,751,997 A | 6/1988 | Hirsch | | 5,435,802 A | 7/1995 | Kober |
| 4,753,429 A | 6/1988 | Irvine et al. | | 5,449,353 A | 9/1995 | Watanabe et al. |
| 4,756,141 A | 7/1988 | Hirsch et al. | | 5,464,401 A | 11/1995 | Hasse et al. |
| 4,764,325 A | 8/1988 | Angstadt | | 5,486,253 A | 1/1996 | Otruba |
| 4,765,780 A | 8/1988 | Angstadt | | 5,494,622 A | 2/1996 | Heath et al. |
| 4,776,920 A | 10/1988 | Ryan | | 5,500,075 A | 3/1996 | Herrmann |
| 4,777,513 A | 10/1988 | Nelson | | 5,516,392 A | 5/1996 | Bridges et al. |
| 4,782,647 A | 11/1988 | Williams et al. | | 5,518,566 A | 5/1996 | Bridges et al. |
| 4,785,986 A | 11/1988 | Daane et al. | | 5,525,175 A | 6/1996 | Blenke et al. |
| 4,795,510 A | 1/1989 | Wittrock et al. | | 5,531,850 A | 7/1996 | Herrmann |
| 4,798,353 A | 1/1989 | Peugh | | 5,540,647 A | 7/1996 | Weiermann et al. |
| 4,801,345 A | 1/1989 | Dussaud et al. | | 5,545,275 A | 8/1996 | Herrin et al. |
| 4,802,570 A | 2/1989 | Hirsch et al. | | 5,545,285 A | 8/1996 | Johnson |
| 4,840,609 A | 6/1989 | Jones et al. | | 5,552,013 A | 9/1996 | Ehlert et al. |
| 4,845,964 A | 7/1989 | Bors et al. | | 5,556,360 A | 9/1996 | Kober et al. |
| 4,864,802 A | 9/1989 | D'Angelo | | 5,556,504 A | 9/1996 | Rajala et al. |
| 4,880,102 A | 11/1989 | Indrebo | | 5,560,793 A | 10/1996 | Ruscher et al. |
| 4,888,231 A | 12/1989 | Angstadt | | 5,575,187 A | 11/1996 | Dieterlen |
| 4,892,536 A | 1/1990 | Des Marais et al. | | 5,586,964 A | 12/1996 | Chase |
| 4,904,440 A | 2/1990 | Angstadt | | 5,602,747 A | 2/1997 | Rajala |
| 4,908,175 A | 3/1990 | Angstadt | | 5,603,794 A | 2/1997 | Thomas |
| 4,909,019 A | 3/1990 | Delacretaz et al. | | 5,624,420 A | 4/1997 | Bridges et al. |
| 4,915,767 A | 4/1990 | Rajala et al. | | 5,624,428 A | 4/1997 | Sauer |
| 4,917,746 A | 4/1990 | Kons | | 5,628,738 A | 5/1997 | Suekane |
| 4,925,520 A | 5/1990 | Beaudoin et al. | | 5,634,917 A | 6/1997 | Fujioka et al. |
| 4,927,322 A | 5/1990 | Schweizer et al. | | 5,643,165 A | 7/1997 | Klekamp |
| 4,927,486 A | 5/1990 | Fattal et al. | | 5,643,396 A | 7/1997 | Rajala et al. |
| 4,927,582 A | 5/1990 | Bryson | | 5,645,543 A | 7/1997 | Nomura et al. |
| 4,937,887 A | 7/1990 | Schreiner | | 5,659,229 A | 8/1997 | Rajala |
| 4,963,072 A | 10/1990 | Miley et al. | | 5,660,657 A | 8/1997 | Rajala et al. |
| 4,987,940 A | 1/1991 | Straub et al. | | 5,660,665 A | 8/1997 | Jalonen |
| 4,994,010 A | 2/1991 | Doderer-Winkler | | 5,683,376 A | 11/1997 | Kato et al. |
| 5,000,806 A | 3/1991 | Merkatoris et al. | | 5,683,531 A | 11/1997 | Roessler et al. |
| 5,021,111 A | 6/1991 | Swenson | | RE35,687 E | 12/1997 | Igaue et al. |
| 5,025,910 A | 6/1991 | Lasure et al. | | 5,693,165 A | 12/1997 | Schmitz |
| 5,045,039 A | 9/1991 | Bay | | 5,699,653 A | 12/1997 | Hartman et al. |
| 5,062,597 A | 11/1991 | Martin et al. | | 5,705,013 A | 1/1998 | Nease |
| 5,064,179 A | 11/1991 | Martin | | 5,707,470 A | 1/1998 | Rajala et al. |
| 5,064,492 A | 11/1991 | Friesch | | 5,711,832 A | 1/1998 | Glaug et al. |
| 5,080,741 A | 1/1992 | Nomura et al. | | 5,725,518 A | 3/1998 | Coates |
| 5,094,658 A | 3/1992 | Smithe et al. | | 5,725,714 A | 3/1998 | Fujioka |
| 5,096,532 A | 3/1992 | Neuwirth et al. | | 5,743,994 A | 4/1998 | Roessler et al. |
| 5,108,017 A | 4/1992 | Adamski, Jr. et al. | | 5,745,922 A | 5/1998 | Rajala et al. |
| 5,109,767 A | 5/1992 | Nyfeler et al. | | 5,746,869 A | 5/1998 | Hayden et al. |
| 5,110,403 A | 5/1992 | Ehlert | | 5,749,989 A | 5/1998 | Linman et al. |
| 5,127,981 A | 7/1992 | Straub et al. | | 5,766,389 A | 6/1998 | Brandon et al. |
| 5,131,525 A | 7/1992 | Musschoot | | 5,788,797 A | 8/1998 | Herrin et al. |
| 5,131,901 A | 7/1992 | Moll | | 5,817,199 A | 10/1998 | Brennecke et al. |
| 5,133,511 A | 7/1992 | Mack | | 5,829,164 A | 11/1998 | Kotitschke |
| 5,147,487 A | 9/1992 | Nomura et al. | | 5,836,931 A | 11/1998 | Toyoda et al. |
| 5,163,594 A | 11/1992 | Meyer | | 5,858,012 A | 1/1999 | Yamaki et al. |
| 5,171,239 A | 12/1992 | Igaue et al. | | 5,865,393 A | 2/1999 | Kreft et al. |
| 5,176,244 A | 1/1993 | Radzins et al. | | 5,868,727 A | 2/1999 | Barr et al. |
| 5,183,252 A | 2/1993 | Wolber et al. | | 5,876,027 A | 3/1999 | Fukui et al. |
| 5,188,627 A | 2/1993 | Igaue et al. | | 5,876,792 A | 3/1999 | Caldwell |
| 5,190,234 A | 3/1993 | Ezekiel | | 5,879,500 A | 3/1999 | Herrin et al. |
| 5,195,684 A | 3/1993 | Radzins | | 5,902,431 A | 5/1999 | Wilkinson et al. |
| 5,203,043 A | 4/1993 | Riedel | | 5,932,039 A | 8/1999 | Popp et al. |
| 5,213,645 A | 5/1993 | Nomura et al. | | 5,938,193 A | 8/1999 | Bluemle et al. |
| 5,222,422 A | 6/1993 | Benner, Jr. et al. | | 5,964,390 A | 10/1999 | Borresen et al. |
| 5,223,069 A | 6/1993 | Tokuno et al. | | 5,964,970 A | 10/1999 | Woolwine et al. |

| | | | | | | |
|---|---|---|---|---|---|---|
| 6,036,805 A | 3/2000 | McNichols | | 6,893,528 B2 | 5/2005 | Middelstadt et al. |
| 6,043,836 A | 3/2000 | Kerr et al. | | 6,913,718 B2 | 7/2005 | Ducker |
| 6,050,517 A | 4/2000 | Dobrescu et al. | | 6,918,404 B2 | 7/2005 | Dias da Silva |
| 6,074,110 A | 6/2000 | Verlinden et al. | | 6,976,521 B2 | 12/2005 | Mlinar |
| 6,076,442 A | 6/2000 | Arterburn et al. | | 6,978,486 B2 | 12/2005 | Zhou et al. |
| 6,098,249 A | 8/2000 | Toney et al. | | 7,017,820 B1 | 3/2006 | Brunner |
| 6,123,792 A | 9/2000 | Samida et al. | | 7,045,031 B2 | 5/2006 | Popp et al. |
| 6,171,432 B1 | 1/2001 | Brisebois | | 7,066,586 B2 | 6/2006 | da Silva |
| 6,183,576 B1 | 2/2001 | Couillard et al. | | 7,077,393 B2 | 7/2006 | Ishida |
| 6,195,850 B1 | 3/2001 | Melbye | | 7,130,710 B2 | 10/2006 | Popp et al. |
| 6,210,386 B1 | 4/2001 | Inoue | | 7,172,666 B2 | 2/2007 | Groves et al. |
| 6,212,859 B1 | 4/2001 | Bielik, Jr. et al. | | 7,195,684 B2 | 3/2007 | Satoh |
| 6,214,147 B1 | 4/2001 | Mortellite et al. | | 7,201,345 B2 | 4/2007 | Werner |
| 6,250,048 B1 | 6/2001 | Linkiewicz | | 7,214,174 B2 | 5/2007 | Allen et al. |
| 6,264,784 B1 | 7/2001 | Menard et al. | | 7,214,287 B2 | 5/2007 | Shiomi |
| 6,276,421 B1 | 8/2001 | Valenti et al. | | 7,247,219 B2 | 7/2007 | O'Dowd |
| 6,276,587 B1 | 8/2001 | Boerresen | | 7,303,708 B2 | 12/2007 | Andrews et al. |
| 6,284,081 B1 | 9/2001 | Vogt et al. | | 7,380,213 B2 | 5/2008 | Pokorny et al. |
| 6,287,409 B1 | 9/2001 | Stephany | | 7,398,870 B2 | 7/2008 | McCabe |
| 6,306,122 B1 | 10/2001 | Narawa et al. | | 7,449,084 B2 | 11/2008 | Nakakado |
| 6,309,336 B1 | 10/2001 | Muessig et al. | | 7,452,436 B2 | 11/2008 | Andrews |
| 6,312,420 B1 | 11/2001 | Sasaki et al. | | 7,533,709 B2 | 5/2009 | Meyer |
| 6,314,333 B1 | 11/2001 | Rajala et al. | | 7,537,215 B2 | 5/2009 | Beaudoin et al. |
| 6,315,022 B1 | 11/2001 | Herrin et al. | | 7,587,966 B2 | 9/2009 | Nakakado et al. |
| 6,319,347 B1 | 11/2001 | Rajala | | 7,618,513 B2 | 11/2009 | Meyer |
| 6,336,921 B1 | 1/2002 | Kato et al. | | 7,638,014 B2 | 12/2009 | Coose et al. |
| 6,358,350 B1 | 3/2002 | Glaug et al. | | 7,640,962 B2 | 1/2010 | Meyer et al. |
| 6,369,291 B1 | 4/2002 | Uchimoto et al. | | 7,703,599 B2 | 4/2010 | Meyer |
| 6,375,769 B1 | 4/2002 | Quereshi et al. | | 7,708,849 B2 | 5/2010 | McCabe |
| 6,391,013 B1 | 5/2002 | Suzuki et al. | | 7,770,712 B2 | 8/2010 | McCabe |
| 6,416,697 B1 | 7/2002 | Venturino et al. | | 7,771,407 B2 | 8/2010 | Umebayashi |
| 6,431,038 B2 | 8/2002 | Couturier | | 7,780,052 B2 | 8/2010 | McCabe |
| 6,440,246 B1 | 8/2002 | Vogt et al. | | 7,811,403 B2 | 10/2010 | Andrews |
| 6,443,389 B1 | 9/2002 | Palone | | 7,861,756 B2 | 1/2011 | Jenquin et al. |
| 6,446,795 B1 | 9/2002 | Allen et al. | | 7,909,956 B2 | 3/2011 | Coose et al. |
| 6,473,669 B2 | 10/2002 | Rajala et al. | | 7,975,584 B2 | 7/2011 | McCabe |
| 6,475,325 B1 | 11/2002 | Parrish et al. | | 7,987,964 B2 | 8/2011 | McCabe |
| 6,478,786 B1 | 11/2002 | Glaug et al. | | 8,007,484 B2 | 8/2011 | McCabe et al. |
| 6,482,278 B1 | 11/2002 | McCabe et al. | | 8,007,623 B2 | 8/2011 | Andrews |
| 6,494,244 B2 | 12/2002 | Parrish et al. | | 8,011,493 B2 | 9/2011 | Giuliani et al. |
| 6,514,233 B1 | 2/2003 | Glaug | | 8,016,972 B2 | 9/2011 | Andrews et al. |
| 6,521,320 B2 | 2/2003 | McCabe et al. | | 2001/0012813 A1 | 8/2001 | Bluemle |
| 6,523,595 B1 | 2/2003 | Milner et al. | | 2001/0017181 A1 | 8/2001 | Otruba et al. |
| 6,524,423 B1 | 2/2003 | Hilt et al. | | 2002/0046802 A1 | 4/2002 | Tachibana et al. |
| 6,533,879 B2 | 3/2003 | Quereshi et al. | | 2002/0059013 A1 | 5/2002 | Rajala et al. |
| 6,540,857 B1 | 4/2003 | Coenen et al. | | 2002/0096241 A1 | 7/2002 | Instance |
| 6,547,909 B1 | 4/2003 | Butterworth | | 2002/0125105 A1 | 9/2002 | Nakakado |
| 6,551,228 B1 | 4/2003 | Richards | | 2002/0162776 A1 | 11/2002 | Hergeth |
| 6,551,430 B1 | 4/2003 | Glaug et al. | | 2003/0000620 A1 | 1/2003 | Herrin et al. |
| 6,554,815 B1 | 4/2003 | Umebayashi | | 2003/0015209 A1 | 1/2003 | Gingras et al. |
| 6,569,275 B1 | 5/2003 | Popp et al. | | 2003/0051802 A1 | 3/2003 | Hargett et al. |
| 6,572,520 B2 | 6/2003 | Blumle | | 2003/0052148 A1 | 3/2003 | Rajala et al. |
| 6,581,517 B1 | 6/2003 | Becker et al. | | 2003/0066585 A1 | 4/2003 | McCabe |
| 6,585,841 B1 | 7/2003 | Popp et al. | | 2003/0083638 A1 | 5/2003 | Molee |
| 6,589,149 B1 | 7/2003 | VanEperen et al. | | 2003/0084984 A1 | 5/2003 | Glaug et al. |
| 6,596,108 B2 | 7/2003 | McCabe | | 2003/0089447 A1 | 5/2003 | Molee et al. |
| 6,605,172 B1 | 8/2003 | Anderson et al. | | 2003/0121614 A1 | 7/2003 | Tabor et al. |
| 6,605,173 B2 | 8/2003 | Glaug et al. | | 2003/0135189 A1 | 7/2003 | Umebayashi |
| 6,637,583 B1 | 10/2003 | Andersson | | 2004/0007328 A1 | 1/2004 | Popp et al. |
| 6,648,122 B1 | 11/2003 | Hirsch et al. | | 2004/0016500 A1 | 1/2004 | Tachibana et al. |
| 6,649,010 B2 | 11/2003 | Parrish et al. | | 2004/0044325 A1 | 3/2004 | Corneliusson |
| 6,656,309 B1 | 12/2003 | Parker et al. | | 2004/0087425 A1 | 5/2004 | Ng et al. |
| 6,659,150 B1 | 12/2003 | Perkins et al. | | 2004/0112517 A1 | 6/2004 | Groves et al. |
| 6,659,991 B2 | 12/2003 | Suckane | | 2004/0164482 A1 | 8/2004 | Edinger |
| 6,675,552 B2 | 1/2004 | Kunz et al. | | 2004/0182497 A1 | 9/2004 | Lowrey |
| 6,684,925 B2 | 2/2004 | Nagate et al. | | 2005/0000628 A1 | 1/2005 | Norrby |
| 6,722,494 B2 | 4/2004 | Nakakado | | 2005/0022476 A1 | 2/2005 | Hamer |
| 6,730,189 B1 | 5/2004 | Franzmann | | 2005/0139713 A1 | 6/2005 | Weber et al. |
| 6,743,324 B2 | 6/2004 | Hargett et al. | | 2005/0196538 A1 | 9/2005 | Sommer et al. |
| 6,750,466 B2 | 6/2004 | Guha et al. | | 2005/0230056 A1 | 10/2005 | Meyer et al. |
| 6,758,109 B2 | 7/2004 | Nakakado | | 2005/0230449 A1 | 10/2005 | Meyer et al. |
| 6,766,817 B2 | 7/2004 | da Silva | | 2005/0233881 A1 | 10/2005 | Meyer |
| 6,808,582 B2 | 10/2004 | Popp et al. | | 2005/0234412 A1 | 10/2005 | Andrews et al. |
| D497,991 S | 11/2004 | Otsubo et al. | | 2005/0257881 A1 | 11/2005 | Coose et al. |
| 6,820,671 B2 | 11/2004 | Calvert | | 2005/0275148 A1 | 12/2005 | Beaudoin et al. |
| 6,837,840 B2 | 1/2005 | Yonekawa et al. | | 2006/0021300 A1 | 2/2006 | Tada et al. |
| 6,840,616 B2 | 1/2005 | Summers | | 2006/0137298 A1 | 6/2006 | Oshita et al. |
| 6,852,186 B1 | 2/2005 | Matsuda et al. | | 2006/0224137 A1 | 10/2006 | McCabe et al. |
| 6,875,202 B2 | 4/2005 | Kumasaka et al. | | 2006/0265867 A1 | 11/2006 | Schaap |

| | | | | | | |
|---|---|---|---|---|---|---|
| 2007/0074953 | A1 | 4/2007 | McCabe | FR | 2255961 | 7/1975 |
| 2008/0077418 | A1 | 3/2008 | Coleman | FR | 1132325 | 10/2006 |
| 2008/0223537 | A1 | 9/2008 | Wiedmann | FR | 2891811 | 4/2007 |
| 2009/0020211 | A1 | 1/2009 | Andrews et al. | GB | 191101501 A | 0/1912 |
| 2010/0078119 | A1 | 4/2010 | Yamamoto | GB | 439897 | 12/1935 |
| 2010/0078120 | A1 | 4/2010 | Otsubo | GB | 856389 | 12/1960 |
| 2010/0078127 | A1 | 4/2010 | Yamamoto | GB | 941073 | 11/1963 |
| 2010/0193138 | A1 | 8/2010 | Eckstein | GB | 1096373 | 12/1967 |
| 2010/0193155 | A1 | 8/2010 | Nakatani | GB | 1126539 | 9/1968 |

FOREIGN PATENT DOCUMENTS

| | | | | | |
|---|---|---|---|---|---|
| GB | 1346329 | 2/1974 |
| CA | 1153345 | 9/1983 | GB | 1412812 | 11/1975 |
| CA | 1190078 | 7/1985 | GB | 2045298 | 10/1980 |
| CA | 1210744 | 9/1986 | GB | 2115775 | 9/1983 |
| CA | 1212132 | 9/1986 | GB | 2288316 | 10/1995 |
| CA | 1236056 | 5/1988 | IT | 1374910 | 5/2010 |
| CA | 1249102 | 1/1989 | IT | 1374911 | 5/2010 |
| CA | 1292201 | 11/1991 | JP | 428364 | 1/1992 |
| CA | 1307244 | 9/1992 | JP | 542180 | 2/1993 |
| CA | 1308015 | 9/1992 | JP | 576566 | 3/1993 |
| CA | 1310342 | 11/1992 | JP | 626160 | 2/1994 |
| CA | 2023816 | 3/1994 | JP | 626161 | 2/1994 |
| CA | 2404154 | 10/2001 | JP | 6197925 A | 7/1994 |
| CA | 2541194 | 10/2006 | JP | 9299398 | 11/1997 |
| CA | 2559517 | 4/2007 | JP | 10035621 | 2/1998 |
| CA | 2337700 | 8/2008 | JP | 10-277091 A | 10/1998 |
| CA | 2407867 | 6/2010 | SE | 0602047 | 5/2007 |
| DE | 60123502 | 10/2006 | SE | 0601003-7 | 6/2007 |
| DE | 60216550 | 12/2006 | SE | 0601145-6 | 10/2009 |
| DE | 102005048868 | 4/2007 | WO | WO 2008155618 | 12/1988 |
| DE | 102006047280 | 4/2007 | WO | WO9403301 | 2/1994 |
| EP | 0044206 | 1/1982 | WO | WO9732552 | 9/1997 |
| EP | 0048011 | 3/1982 | WO | WO9747265 | 12/1997 |
| EP | 0089106 | 9/1983 | WO | WO9747810 | 12/1997 |
| EP | 0099732 | 2/1984 | WO | WO9821134 | 5/1998 |
| EP | 0206208 | 12/1986 | WO | WO9907319 | 2/1999 |
| EP | 0304140 | 2/1989 | WO | WO9913813 A1 | 3/1999 |
| EP | 0439897 | 8/1991 | WO | WO9932385 | 7/1999 |
| EP | 0455231 A1 | 11/1991 | WO | WO9965437 | 12/1999 |
| EP | 510251 | 10/1992 | WO | WO0143682 | 6/2001 |
| EP | 0652175 A1 | 5/1995 | WO | WO0172237 | 10/2001 |
| EP | 0811473 | 12/1997 | WO | WO0172237 A2 | 10/2001 |
| EP | 0901780 | 3/1999 | WO | WO2004007329 | 1/2004 |
| EP | 0990588 | 4/2000 | WO | WO2005075163 | 8/2005 |
| EP | 1132325 A2 | 9/2001 | WO | WO 2007029115 | 3/2007 |
| EP | 1199057 | 4/2002 | WO | WO 2007039800 | 4/2007 |
| EP | 1272347 A0 | 1/2003 | WO | WO 2007/126347 A1 | 11/2007 |
| EP | 1366734 | 12/2003 | WO | WO 2008001209 | 1/2008 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |

OTHER PUBLICATIONS

USPTO Office Action dated Dec. 1, 2010 regarding U.S. Appl. No. 12/383,655, 15 pages.

USPTO Examiner Interview Summary dated Mar. 15, 2011 regarding U.S. Appl. No. 12/383,655, 4 pages.

Applicant's Interview Summary dated Mar. 29, 2011 regarding U.S. Appl. No. 12/383,655, 2 pages.

European Office Action dated Oct. 4, 2010 regarding European Pat. Appln. Serial No. 10250536.9-2124; 2 pages.

Response to European Office Action dated Mar. 28, 2011 regarding European Pat. Appin. Serial No. 10250536.9-2124; 10 pages.

"Reciprocating Mechanisms", Franklin Jones, vol. 1, date unknown, 2 pages.

METHOD FOR PRODUCING ABSORBENT ARTICLE WITH STRETCH FILM SIDE PANEL AND APPLICATION OF INTERMITTENT DISCRETE COMPONENTS OF AN ABSORBENT ARTICLE

RELATED APPLICATION

This application claims the benefit of co-pending U.S. Provisional Application Ser. No. 61/335,018, filed 30 Dec. 2009.

BACKGROUND OF THE INVENTION

This invention relates to an apparatus and method for producing absorbent articles with stretch film side panels. The invention disclosed herein relates to apparatus and methods for waste reduction and improvements to the quality and production in web processing operations, such as diaper manufacturing. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

The current practice in applying a stretchable web such as a poly web to a second web is involved continuously feeding the poly web into the process which results in poly running full length of product, or alternatively, full length of a constructed insert core which is then placed onto a nonwoven-type chassis. Not all machine configurations can be adapted from a full length poly chassis to a poly insert configuration due to space and/or cost restrictions. It should be understood that application of the poly web along the entire length of the product, rather than only where it is useful, increases the amount of poly material which must be utilized. This is a waste of the material resource and adds additional cost to the product. It is therefore desirable to create a lower cost product by putting poly into the product only where it is useful, instead of the complete product.

However, typical slip/cut application of poly patch to a continuous web does not work well because of the elasticity of the poly web. The slip/cut process allows the poly to slip on anvil prior to being cut causing the poly to violently snap back at the moment of cut. This can result in a short patch-long patch output from the slip/cut where one or more of the resulting poly patches are extremely distorted on the carrier web. This result is useless for producing a diaper-type product and would be unacceptable to the consumer. It is therefore desirable to provide an apparatus that can cut patches from a poly web while eliminating the snap back of the poly web material.

SUMMARY OF THE INVENTION

One aspect of the invention is a method including providing a base non-woven layer, and applying thereto a character strip. Next, a stretched film is applied over the character strip/base non-woven laminate, and the stretched film is intermittently bonded to the base non-woven. Next, a cover non-woven is applied intermittently to the stretched film, thereby creating a laminate comprising the previously mentioned components.

In one embodiment, the method comprises providing a plurality of pairs of heated knives about a rotatable body, with vacuum commutation provided thereto. The stretched film is cut while stretched, the film being held to the rotating body by the vacuum commutation ports about the rotating body, until the stretched film is trimmed and the trim removed by a second source of vacuum. In this embodiment, a block is used to push material into the rotating heated knives. In an alternative embodiment, vacuum is applied to the stretchable film to drawn the material against the heated knife, thereby severing the stretchable film.

Advantages to the present invention include fewer materials in the side seam bond sandwich, such as 4 instead of the 6-10 layers currently used. Fewer layers assist and facilitate ultrasonic bonding, and result in a more uniform product, because fewer layers are required to be constructed. In alternative embodiments, the product can be configured with or without a waist band.

In another embodiment, simultaneously with the chassis formation, the insert assembly takes place. The formed insert is combined with the formed chassis web, and after this combination is made, the product can be folded and side seam bonded to form a pant style diaper if desired, or tape tabs and ears can be applied to form a wrap around style diaper.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
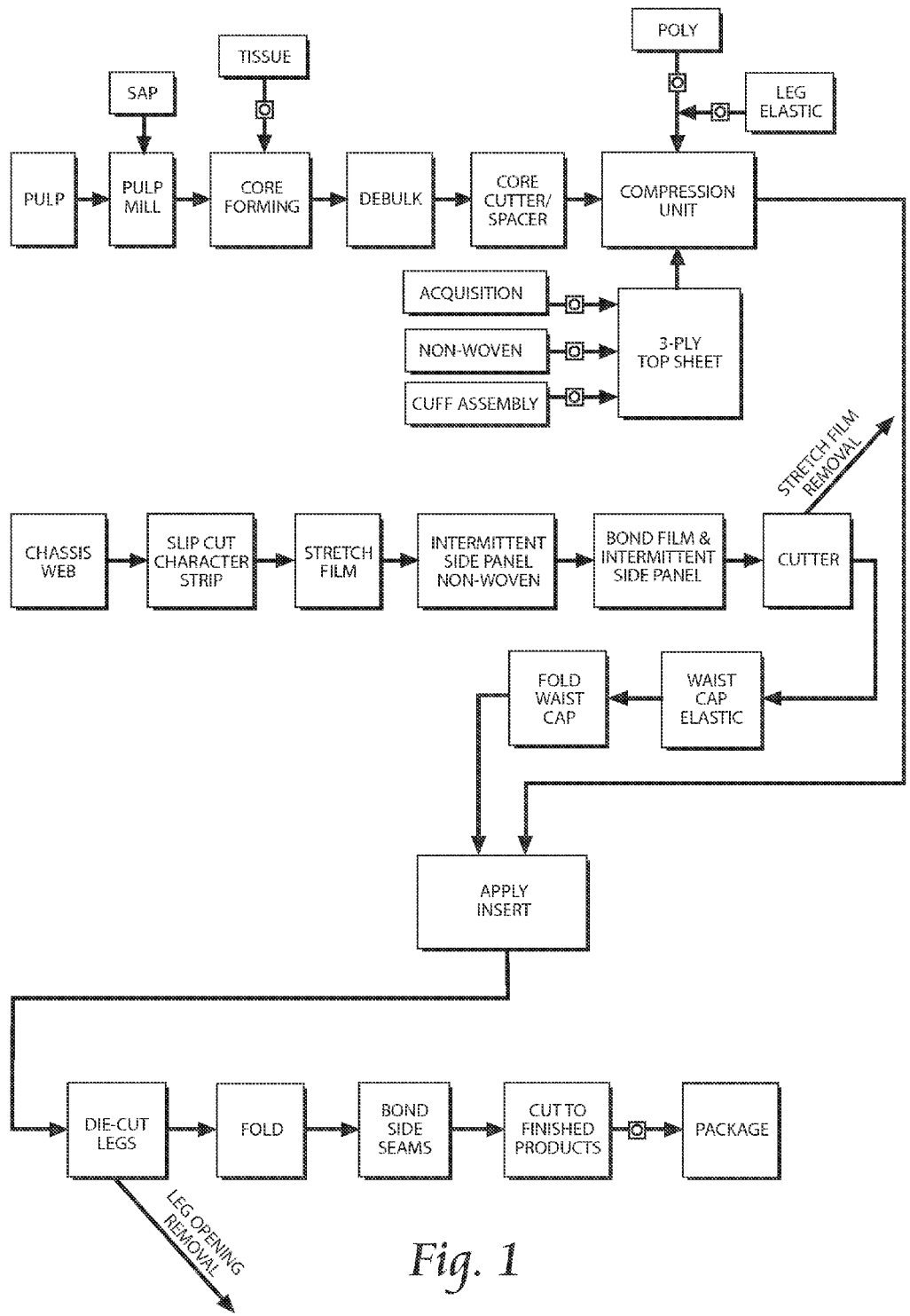
FIG. 1 is a schematic of a representative web processing system.

It is noted that the present techniques and apparatus are described herein with respect to products such as diapers, but as previously mentioned, can be applied to a wide variety of processes in which discrete components are applied sequentially. FIG. 1 describes diaper making generally and schematically.

Referring to FIG. 1, a web processing operation starts with incorporating raw materials such as paper pulp and super absorbent polymer (SAP) in a pulp mill. The mixture is sent to a core forming drum, where cores are formed for retaining liquids. A core can be placed on or within a tissue and processed as shown. Eventually, the tissue layer essentially sandwiches the core, if desired.

The illustrated method displays a core form on tissue method, where the tissue is carried by a core forming drum and the tissue is pulled into a pulp forming pocket, where air-entrained pulp is then drawn into by vacuum.

The process continues through debulking, core cutting and spacing. At a boundary compression unit, the core/tissue combination is sandwiched between a preferably 3-ply topsheet layer and a printed poly backsheet layer carrying leg elastics. The 3-ply topsheet laminate comprises an acquisition layer, designed to accept liquid insult and distribute the over a larger surface of the core to improve absorption performance and also to prevent reverse migration of liquid escaping from the core. Carried between the acquisition layer and the cuff non-woven layer is an insert non-woven layer 80.

At the compression unit, a compression roll compresses the materials around the border of the core, to create a topsheet/backsheet sandwich with the core in the middle of the topsheet and the backseat. At this point, the insert assembly has been formed, and is prepared for introduction to the chassis web assembly shown both on FIG. 1, and also described with regard to FIGS. 8-13 which describe the chassis web assembly. The chassis web assembly can be simultaneously formed in parallel with the insert assembly.

The web can undergo folding, extraction and trimming of excess material, and application of material to tighten the diaper about the waist. Eventually, the product is folded and packaged.

As seen on FIG. 1, the ◯ symbol is shown at locations of introductions of discrete components into the process. At these and other locations of material introduction, inspection can take place to determine the presence or absence of acceptable product introduction. In addition to visual inspection, operational characteristics such as startup/ramp-up/shutdown operations can trigger waste minimization techniques as will be described later.

At each of these operations shown in FIG. 1, diagnostics can be performed to indicate whether the product meets acceptable criteria. If so, discrete elements, such as the core, tissue layers, elastic, etc., continue to be applied in a sequence such as shown in FIG. 1. If not, no additional discrete elements need be applied.

Figure 2:
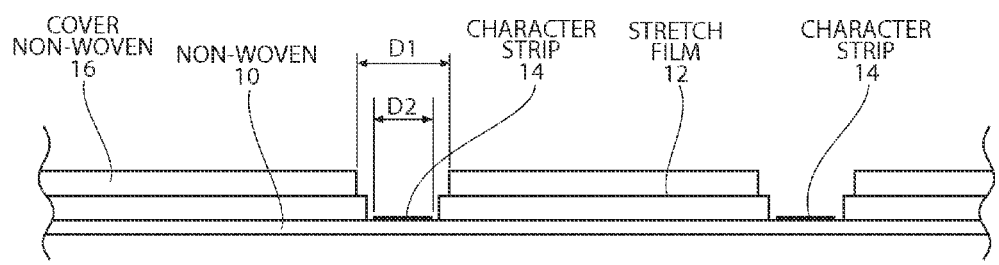
FIG. 2 is a cross-sectional diagram showing a representative product configuration of the present invention.

Referring now to FIG. 2, a cross-sectional diagram showing a representative intended product configuration of the present invention is shown. In this embodiment, it is seen that a first base layer of non-woven material 10 is supplied in continuous fashion. Next, a series of character strips 14 are shown, which for instance can comprise artwork or other design or fashion or useful strips of decorative or non-decorative material. Over the character strips 14 are one or more webs of stretch film 12 which are preferably applied continuously, although intermittent application of stretch film 12 can also be used. Next, a cover-non-woven layer 16 is applied, preferably intermittently and preferably in two webs or lanes of material.

It will be described later that an area of no or little bonding of the stretched film layer 12 to the character strip 14 or base non-woven 10 is achieved across generally the widths D1 and D2. In a preferred embodiment, the width D2 represents the width of character strip 14, and that a wider void space D1 is created over the character strip representative of the distance between intermittent cover non-woven pieces 16.

The area of no or little bonding of the stretched film layer 12 to the character strip 14 or base non-woven 10 is provided so that the stretched film 12 can be severed and removed from the laminate in areas where the stretched film layer 12 is not desired, such as in areas where the stretched film layer 12 has been not or minimally bonded to the other layers of the laminate.

Figure 3:
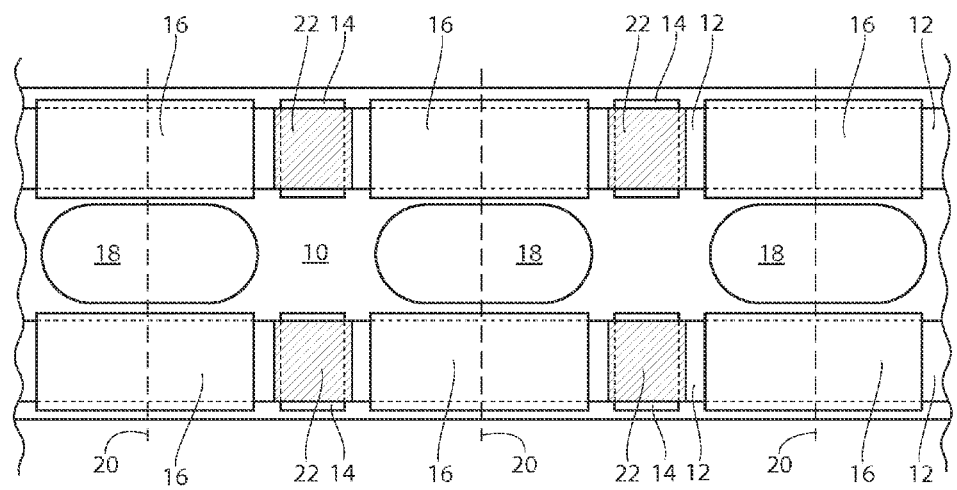
FIG. 3 is a plan view of the laminate produced by a representative web processing system of the present invention prior to introduction of an insert from core forming operations.

Referring now to FIG. 3, a plan view of the preferred laminate produced by a representative web processing system of the present invention is shown.

Leg cutouts 18 can be provided in the base non-woven layer 10 as shown. Side seams 20 are indicated to represent discrete diaper products between successive side seams 20 in the machine direction (right to left or left to right as shown). The character strips 14 can be exposed by severing the stretched film 12 into a removable chip 22 by use of a heated knife applied at areas of roughly equal to or less than width D1 (See FIG. 2) and removing the severed film 22 and exposing the strip 14, which applies a silmu-cut/melt of the stretch film 12 only. This technique is described with reference to FIG. 4, discussed later. It is preferred that the severing of stretch film 12 be just wider than character strip 14, and that little or no bonding will have previously taken place between character strip 14 and the stretched film 12, which will facilitate easy separation of the two elements 12 and 14.

Still referring to FIG. 3, it is preferred that the character the first base layer of non-woven material 10 is supplied in continuous fashion. Next, a series of character strips 14 are applied, preferably in two lanes representing the front and back of the diaper, preferably in the midsection of the diaper when worn by a user. The strips 14 preferably are formed of decorative material, and can also be used as a landing zone for tape tabs or other adhesive mechanisms provided on ears or tape tabs of the diaper (not shown).

In an alternative embodiment (See, e.g., FIG. 12) one or more strands of additional stretchable fabric, such as commercially available Lycra strands of stretchable fabric, can be added to the waist band for added strength if desired. This added fabric can also be applied across the same or narrower regions of the stretch film 12.

In one embodiment, the non-woven 10 is slip-cut to stretched film 12 and bonded ultrasonically or adhesively (not shown). A patterned bonding roll (with vacuum) may be used if desired.

Figure 4:
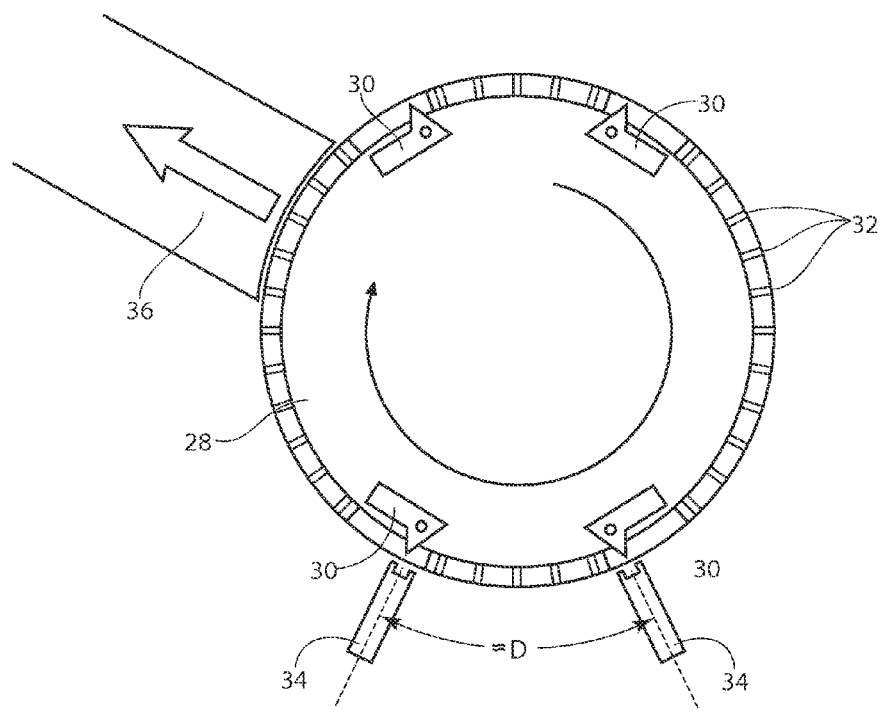
FIG. 4 is a side view of a rotating body used to sever elements and create the laminate of the present invention.

Referring now to FIG. 4, a side view of a rotating body 28 used to sever elements 22 and create the laminate of the present invention is shown. A laminate comprising one or more the elements of the laminate shown in FIG. 2 is introduced to the rotating body 28 (not shown) by conventional means. The laminate is introduced and spaced such that the severing across intended with D1 will be registered to achieve such a cut, by use of knifes 30 spaced apart. The laminate of FIG. 2 will be carried by vacuum commutation ports 32, and the result will be that preferably only the stretch film 12 is severed, and not the base non-woven layer 10. Optionally, the character strip can be severed at this point as well, particularly if the character strip is configured to cut/melt and the same temperature as the stretch film 12, for instance in the range of 225-250° F.

Figure 7:
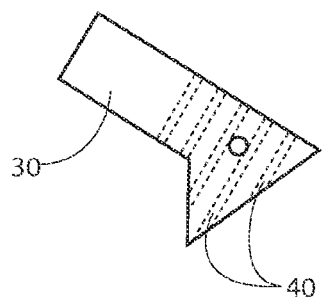
FIG. 7 is a side view of an alternative embodiment of vacuum application to a knife to sever elements of the present invention.

Preferably, the rotating body comprises a series of knifes 30, acting in pairs spaced apart a distance of approximately D1 to act upon the stretch film 12 and sever the stretch film 12 into a chip 22 that will be removed once rotated into communication with vacuum hood 36, which because only stretch film 12 (or, in addition, a small portion of character strip 14) will be removed and discarded or recycled. Preferably, the knives 30 have silicon lagging, heated knives. In this manner, the knifes can be used to heat sever stretch film 12 after being urged into contact with the heated knives by blocks 34, which are used to push the laminate of FIG. 2, including the stretch film material 12 into the rotating heated knives 30. In an alternative embodiment, vacuum is applied to the stretchable film to drawn the material against the heated knife, thereby severing the stretchable film. In an alternate embodiment shown in FIG. 7, the knives 30 can be supplied with vacuum ports 40, which drawn the stretch film into contact with the heated knife blades 30 at desired times to achieve severing the chips 22.

Figure 5:
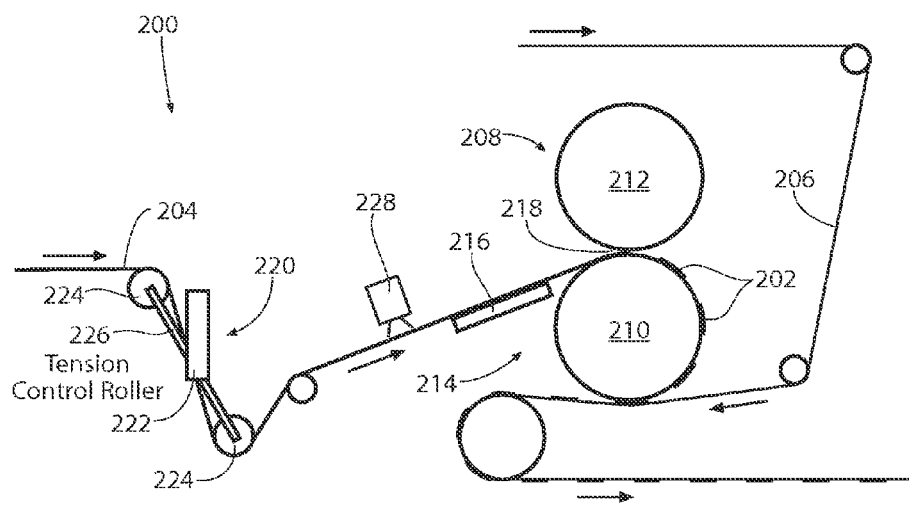
FIG. 5 is a schematic of an embodiment of an apparatus for intermittent application of a web to a target web that may or may not be used in conjunction with the present invention to intermittently apply discrete components.

Optionally, each of the components capable of discrete attachment, such as cover non-woven 16, character strip 14, or stretch film 12, can be applied intermittently using the technique described in relation to the methods and apparatus shown in FIGS. 5-6 below. Referring now to FIG. 5, a diagrammatic view of a zero-waste system 200 for intermittently applying segments 202 of a stretchable material to a target web 206 is shown. The intermittent poly application apparatus and method can be employed at locations of desired intermittent introduction of material to create the laminate shown in FIG. 3. The intermittent poly application apparatus and method can also be used on other, non-poly application processes where intermittent application of a certain component is desired.

As shown in FIG. 5 the apparatus 200 preferably includes a first continuous web 204 of stretchable material. The stretchable material may be of any type known in the art including, but not limited to a poly material. The system 200 further includes a second continuous web 206. The second continuous web 206 is preferably of a nonwoven material. The first continuous web 204 is cut into segments 202 and applied to the second continuous web 206.

The system 200 preferably includes a cutting apparatus 208 for cutting the first continuous web 204 into segments 202. The cutting apparatus may take any form known in the art.

Accumulator 220 can take any form, such as a servo driven roller that speeds up and slows down, an alternate roller configuration, a rocking roller configuration such as shown in FIG. 5, or any different means of accumulating the web, such as a miniature accumulator, or a device similar to a diaper cross-folder, or a tucker blade. A similar blade with low inertia could also be employed.

In the illustrated embodiment the cutting apparatus 208 includes an anvil 210 and a knife roll 212. The anvil 210 is preferably a vacuum anvil. As shown in FIG. 5, the first web 204 of material fed against the anvil 210 surface and is cut into segments 202 by the knife roll 212.

The system 200 preferably includes a rate adjustment apparatus 214. The rate adjustment apparatus 214 is sized and configured to adjust the rate at which the first web 204 is being fed to the anvil 210 while the rate at which the first web 204 is fed to the rate adjustment apparatus 214 remains the same. In the illustrated embodiment, the rate adjustment apparatus 214 takes the form of an infeed conveyor 216 which controls the feed rate of the first web 204 to the anvil 210.

Preferably, after each segment 202 is cut, the infeed of first web 204 to the anvil 210 is momentarily halted. After an appropriate amount of time has passed, the infeed of the first web 204 to the anvil 210 is resumed. In this manner, the segments 202 may be spaced apart when placed on the second web 206. It is contemplated that the leading edge 218 of the first web 204 will engage at least a portion of the vacuum anvil 210 after each segment 202 is cut. Preferably, the vacuum anvil 210 is provided with a relatively low amount of vacuum at that point. The vacuum is preferably sufficient to retain the leading edge 218 of the first web 204 in position, with the anvil 210 slipping below the first web 204. However, the vacuum must be low enough that it does not stretch the first web 204. It should be understood that this may achieved using any means known in the art including, but not limited to a vacuum manifold.

In a preferred embodiment, after the cut is performed at anvil 210, the supply of incoming web 204 to the anvil 218 is momentarily stalled, which results in a gap between supply of the discrete pieces of material 202 to the web 206. Preferably next, the incoming web 204 is then accelerated to feed material to match or nearly match the velocity of roll 210 until the next cut is made. In this sense, the accumulator 220 is used to create the intermittency. The purpose of the speeding and stalling is to prevent snap back of the incoming web 204.

It is further contemplated that the system 200 may include a tension control device 220. The tension control device 220 is preferably sized and configured to eliminate tension in the first web 204 prior to cutting a segment 202 from the first web 204. In this manner when the cut is made the material will not snap back as it would if the first web 204 were under tension. In the illustrated embodiment the tension control device 220 takes the form of a web accumulator 222. However, it is contemplated that the tension control device 220 could take any form known in the art capable of performing such a function. The tension control device 220 of the illustrated embodiment includes a pair of rollers 224 coupled to a pivoting member 226. The pivoting member 226 is pivotable between a first and second position. In this manner, the first web 204 is accumulated in the tension control device 220 when the rate adjustment apparatus 214 momentarily halts the infeed of the web 204 to the anvil 210 as described above.

It is contemplated that the segments 202 may be secured to the target web 206 in any manner known in the art. For example, and not by way of limitation, an adhesive may be applied to the surface of the first web 204 prior to cutting the poly web into segments as shown in FIG. 5. In such an embodiment the system preferably includes an adhesive applicator 228 configured to apply adhesive to the outer surface of the first web 204. The adhesive applicator 228 may be of any type known in the art.

Figure 6:
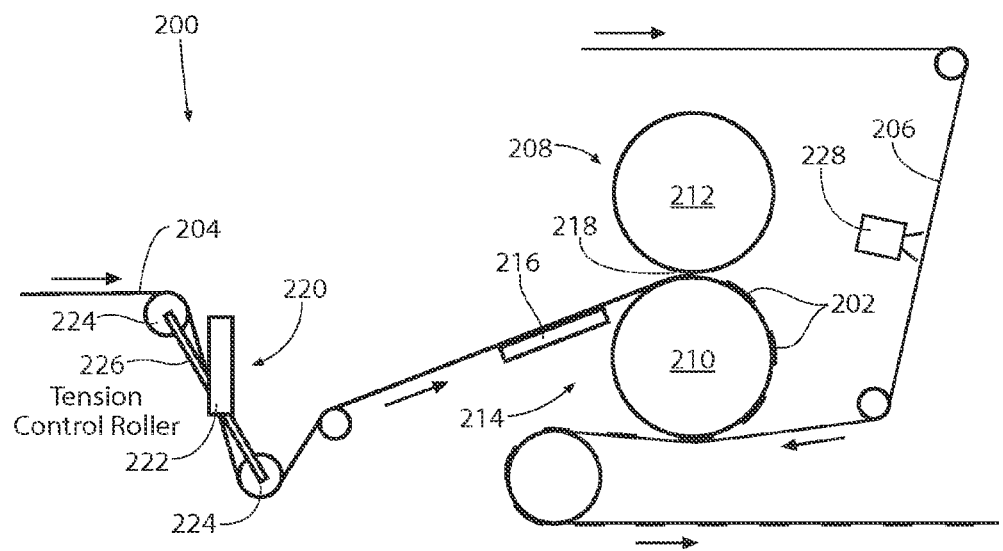
FIG. 6 is an alternative embodiment of an apparatus for intermittent application of a web to a target web.

Alternatively, it is contemplated that adhesive may be applied to the surface of the second web 206 prior to placing the cut segments 202 on the second web 206 as shown in FIG. 6. In such an embodiment the system preferably includes an adhesive applicator 228 configured to apply adhesive to the outer surface of the second web 206. The adhesive applicator 228 may be of any type known in the art.

It is further contemplated that the web segments 202 may be ultrasonically bonded to the second web 206. Bonding positions could be located at positions similar to glue head 228, but also could be repositioned in the system, or could for instance employ roll 210 as an anvil, and equipped with an additional roll to react with roll 210, for instance at the 6 o'clock position of roll 210 (not shown in Figs.) Ultrasonic or heat bonding stations could also be employed.

It is contemplated that the system 200 will provide active tension control and feed approach to change the feed of the first web 204 into the slip/cut cutting apparatus 208 at the moment of cut so the first web 204 is not under tension at the cut moment. This will result in a stable cut segment 202 that can be uniformly applied to the second web 206.

Referring now to FIGS. 8-13 a representative sequence of operations showing manufacturing techniques for a chassis web portion of a product formed according the methods of the present invention is shown. This chassis web portion is intended to be combined with the simultaneously formed core (insert) assembly as described in FIG. 1.

Figure 8:
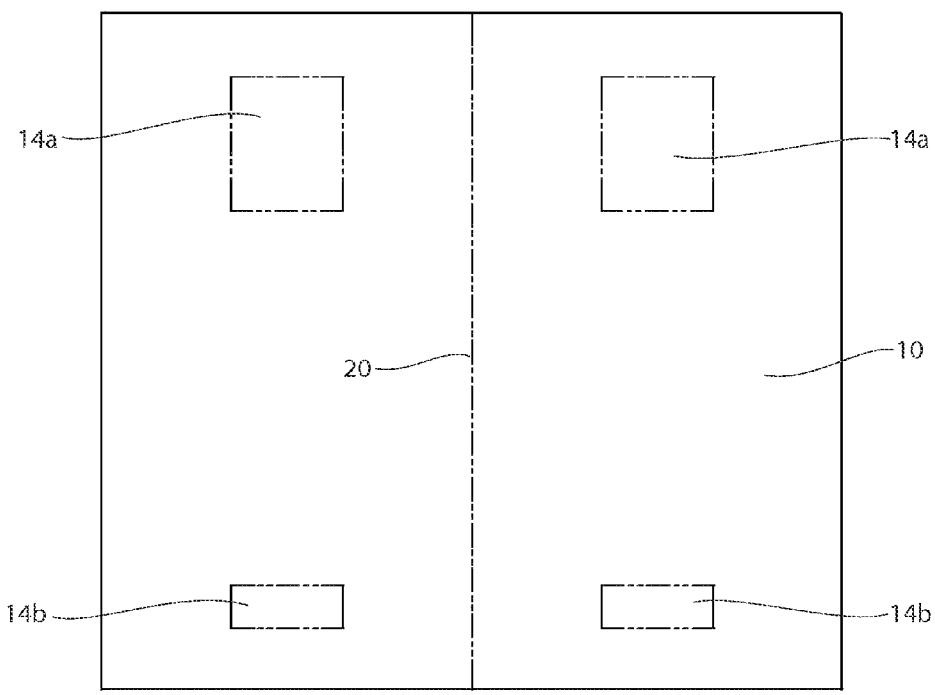
FIGS. 8-17 are a representative sequence of operations showing manufacturing techniques for a product formed according the methods of the present invention.

Beginning with FIG. 8, indicator patch material in front portions 14a and rear portions 14b can be applied, preferably one front patch 14a and one rear patch 14b per product. The indicator patch material 14 is applied to an outer chassis nonwoven material 10. This indicator patch material 14 can be applied (either adhesively, see, e.g., with adhesive 14' on FIG. 19) or printed on the insert. For instance, discrete patches 14a and 14b could be applied to the material 10, or the indicator patches 14 could be printed onto the web 10, or the web 10 could come pre-printed. The indicator patch material 14 is also referred to as a character strip, and this material commonly supplied as artwork and if the product is intended to be a child's disposable product, as a children's oriented art piece.

Figure 9:
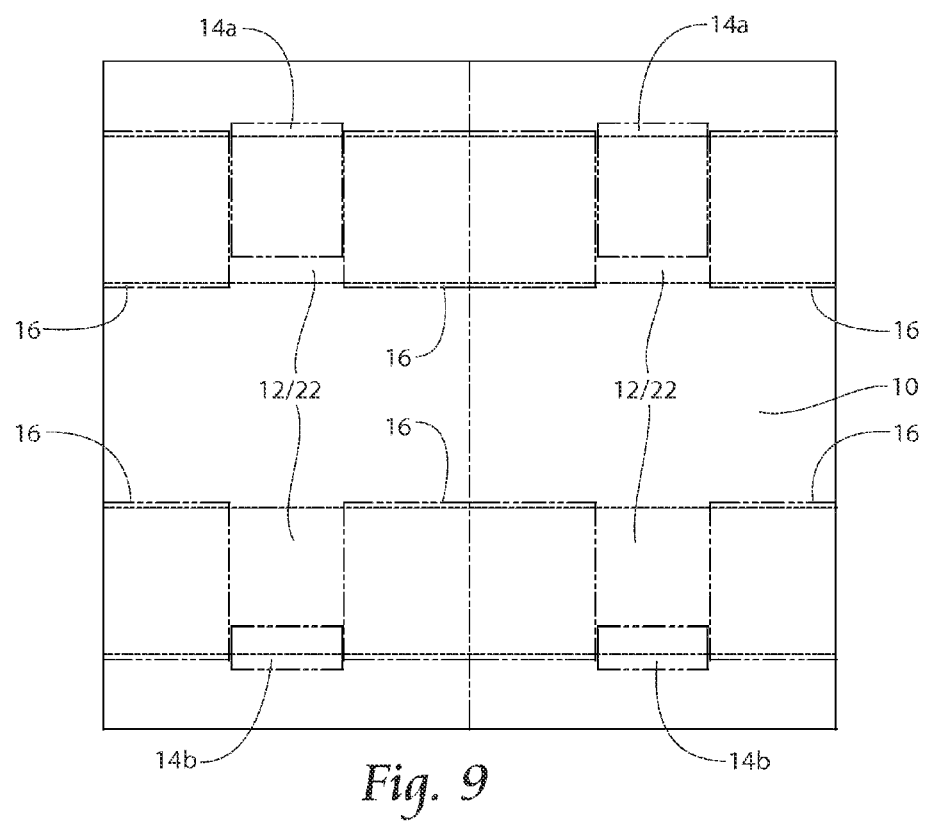

Next, as shown in FIG. 9, continuous layers of film 12 are laid down in the positions shown corresponding to the front and rear of the product when eventually formed, covering portions of the patches 14a and 14b, atop the chassis web 10. The film 12 is preferably stretched to approximately 200%-500% elongation prior to being laid down. Preferably overlying portions of the laid down stretch film 12, an inner chassis non-woven 16 is intermittently applied in the positions shown, again corresponding to the front and rear of the product when formed. Portions of the stretch film 22 comprising chips 22 are removed later in the process from the region generally overlying the indicator patches 14, preferably by use of the hot knife/vacuum procedure depicted in FIG. 4. The inner chassis non-woven 16, also known as the side panel non-woven 16, is preferably applied by slip/cut techniques, but can alternatively be applied intermittently using the mechanism as shown in FIGS. 5-6.

Figure 10:
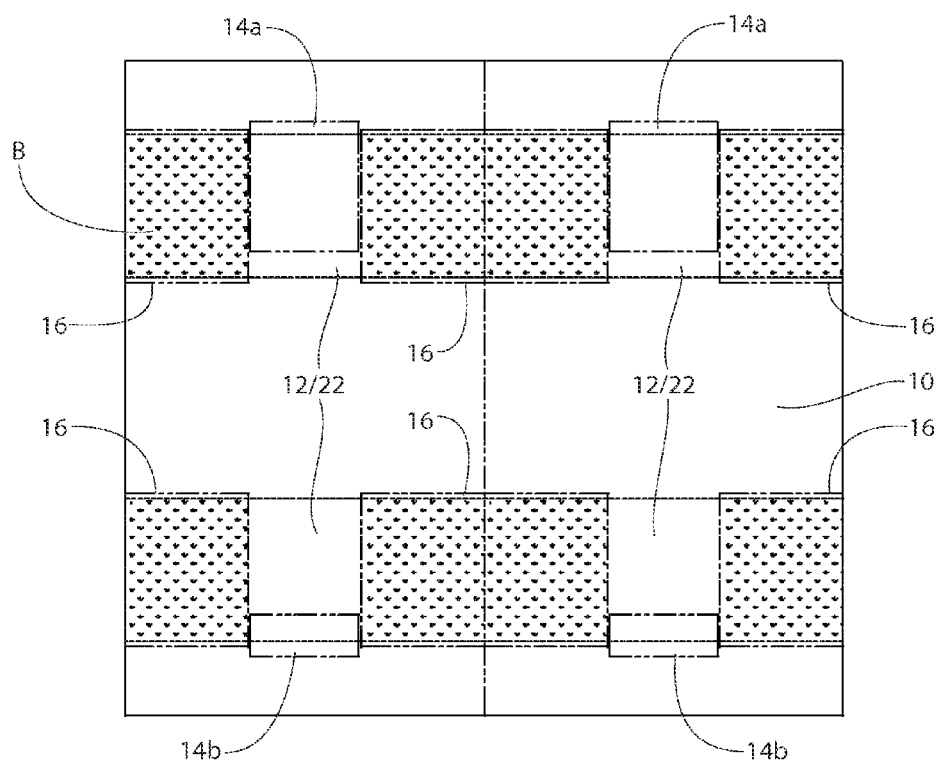
Figure 11:
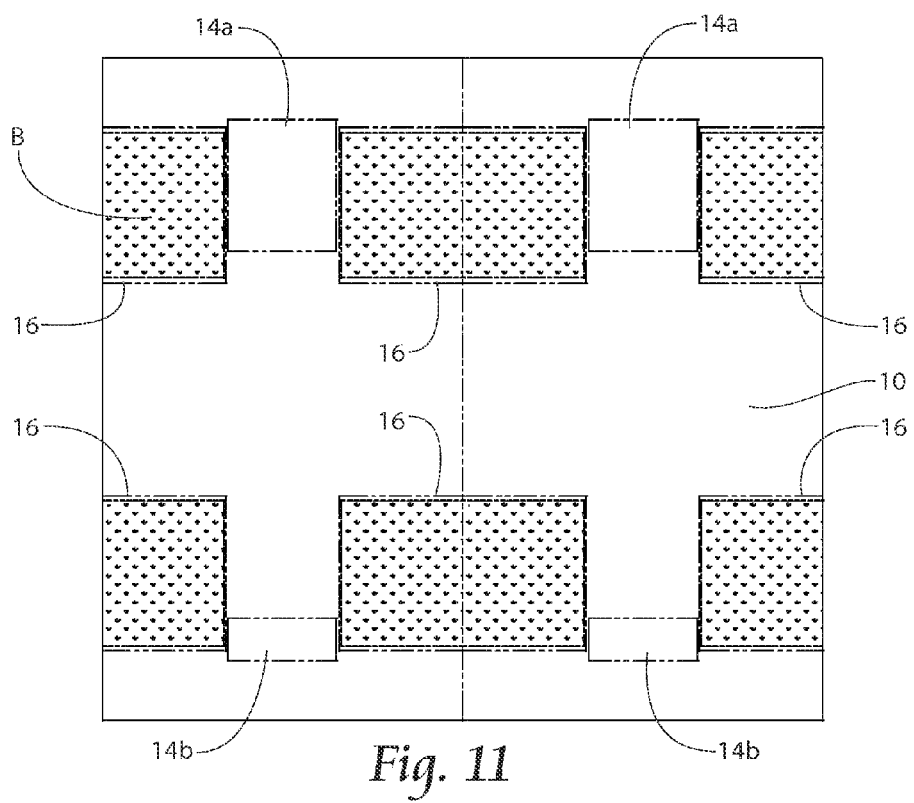

Referring now to FIG. 10, the inner chassis non-woven 16, also known as the side panel non-woven 16 is bonded to the outer chassis nonwoven web 10. The bonding can be accomplished either ultrasonically, mechanically, or adhesively. It is preferred that the bonding pattern be intermittent to coincide with the shape and size of the previously intermittently applied inner-chassis non-woven 16. It is noted that the bond between the inner-chassis non-woven 16 and the outer chassis nonwoven web 10 will also capture the elastic stretch film 12, but only in the portions of the elastic stretch film 12 overlain by the inner-chassis non-woven 16. This allows for the portions of the stretch film 12 between successive intermittently applied inner-chassis non-woven portions 16 to be removed, as shown in FIG. 11, using the hot knife/vacuum procedure depicted in FIG. 4. The elastic film 22 can be cut and removed in the portions previously overlying the indicator patch portions 14, generally between successive intermittently applied inner-chassis non-woven portions 16. This can be accomplished by using a hot knife to sever the stretch film 12 (but none of the material underlying the stretch film 12), and then using a vacuum system to remove the waste chips of the stretch film 12 (not shown).

Figure 12:
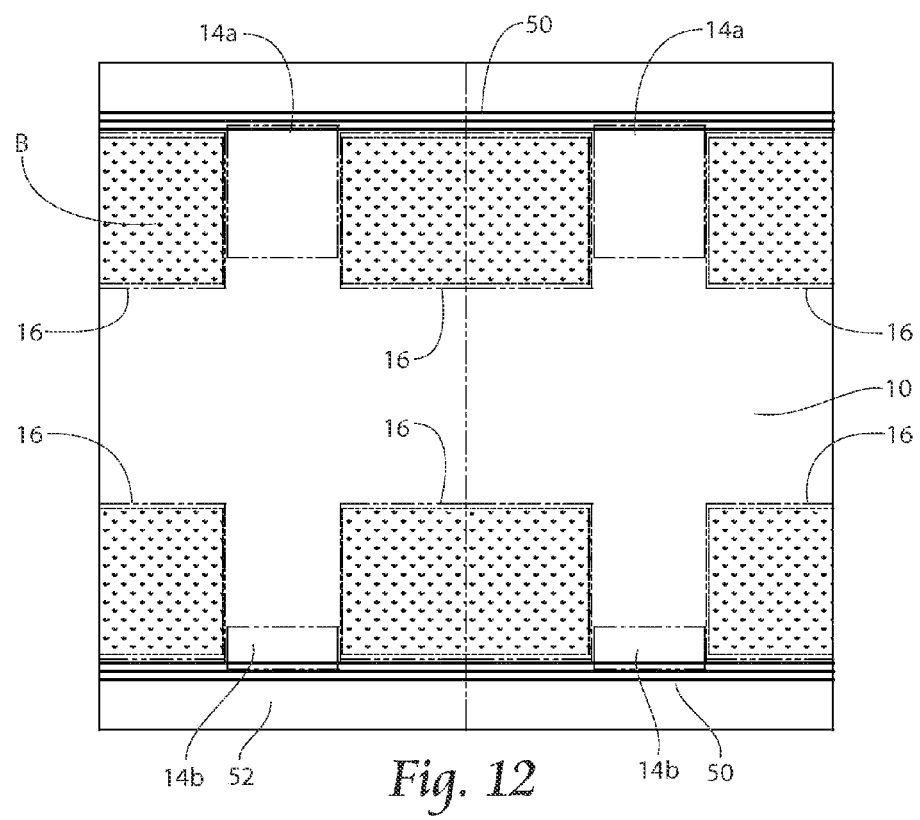
Figure 13:
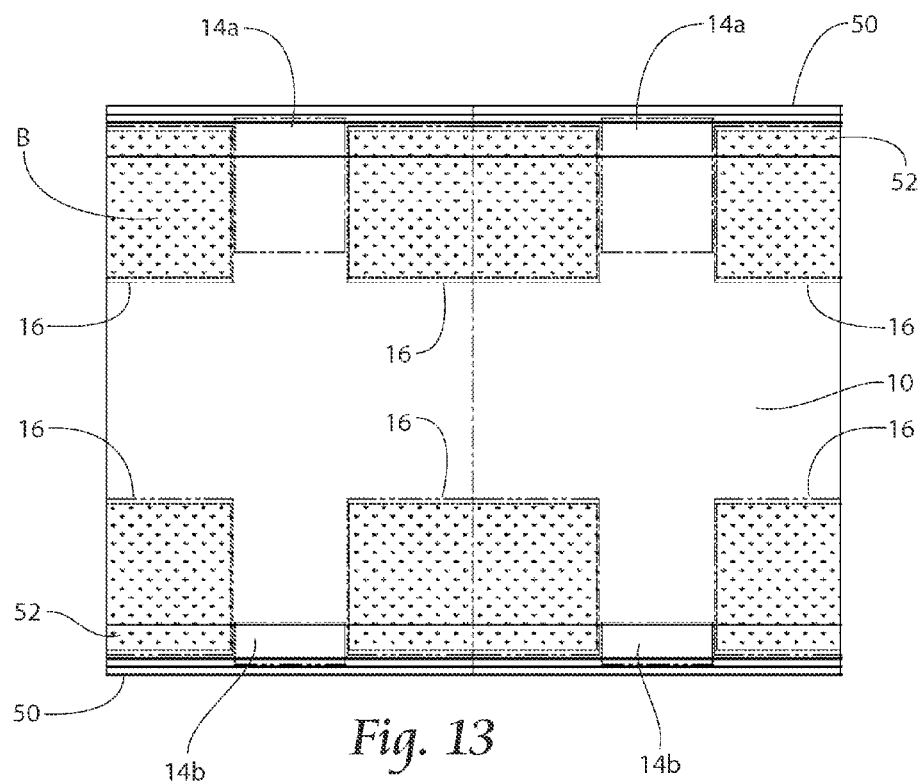
Figure 19:
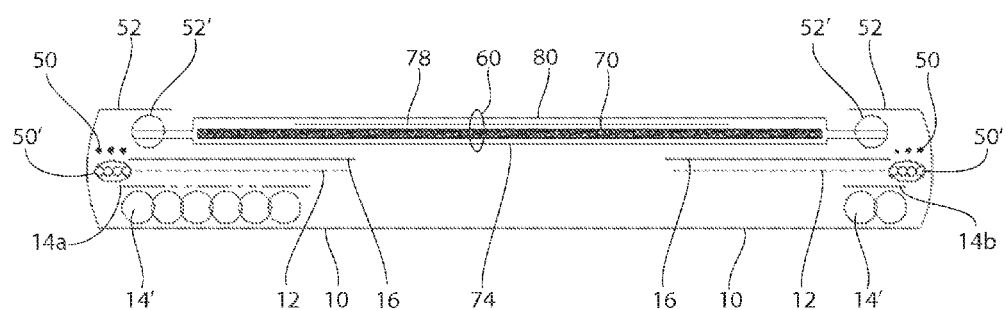
FIG. 19 is a cross-sectional view of a disposable product formed according to methods of the present invention.

Referring now to FIG. 12, strands or bands of waist elastic 50 are placed towards the top and bottom of the web 10, which will ultimately become the front and rear waist band regions in the finished product. The waist elastic 50 can be coupled using adhesive 50' as shown in FIG. 19. The waist elastic 50 is placed away from the waist cap region 52 of the web 10, so that the waist cap region 52 can be folded over and bonded to capture the elastics 50 with the waist cap 52 as shown in FIG. 13.

Figure 14:
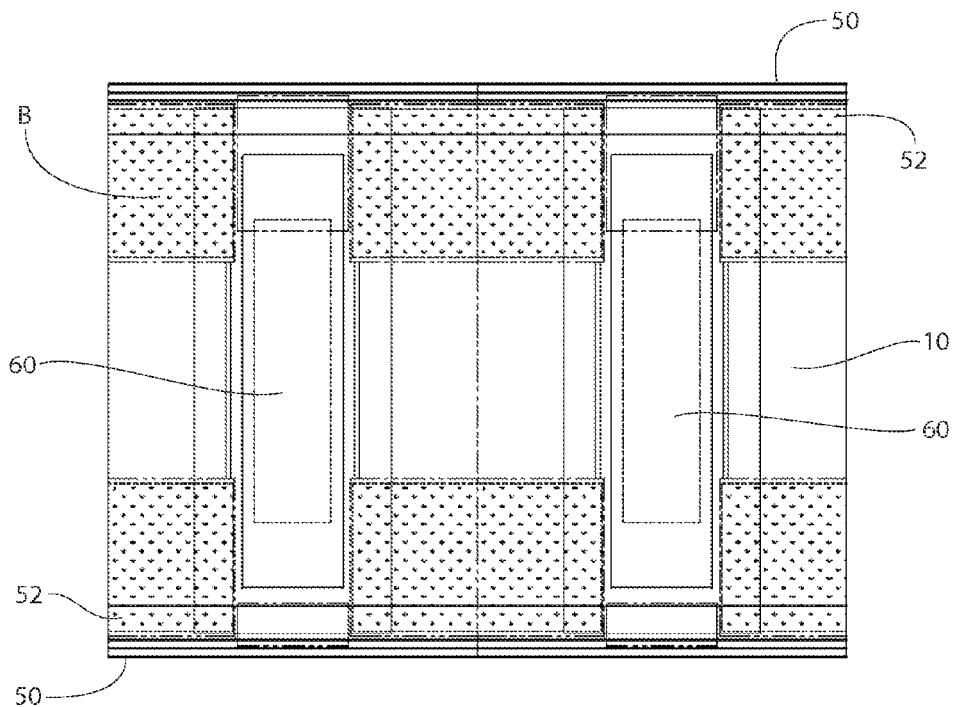
Figure 20:
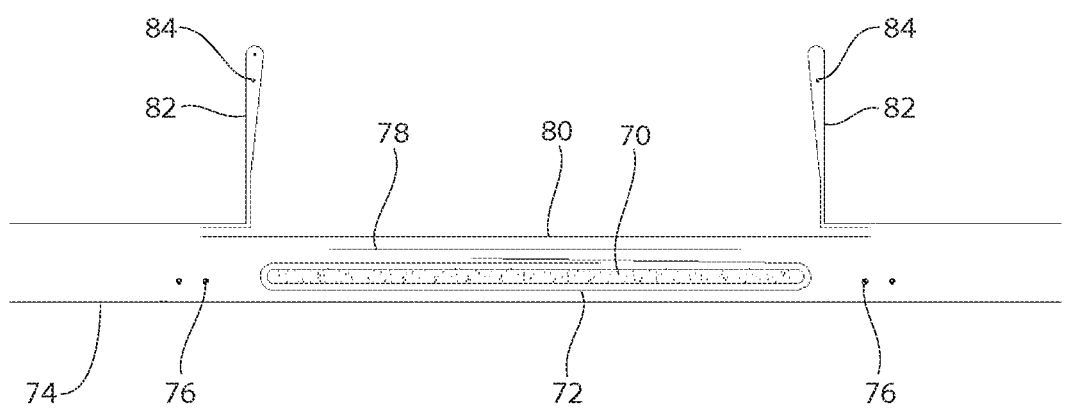
FIG. 20 is a cross-sectional view of a core or insert assembly portion of a disposable product of the present invention; the core being introduced to a simultaneously formed chassis we structure to form a disposable product that can be folded and side seam bonded to form a pant style disposable product.

Referring now to FIG. 14, the previously formed insert assembly 60 (see FIG. 20 for detail on the insert assembly) is introduced to and laid down on the chassis assembly which has been assembled as shown in FIGS. 8-12, in the position show so that the core 60 is generally coincident with the indicator patch portions 14, in the center of the final product once produced.

Figure 15:
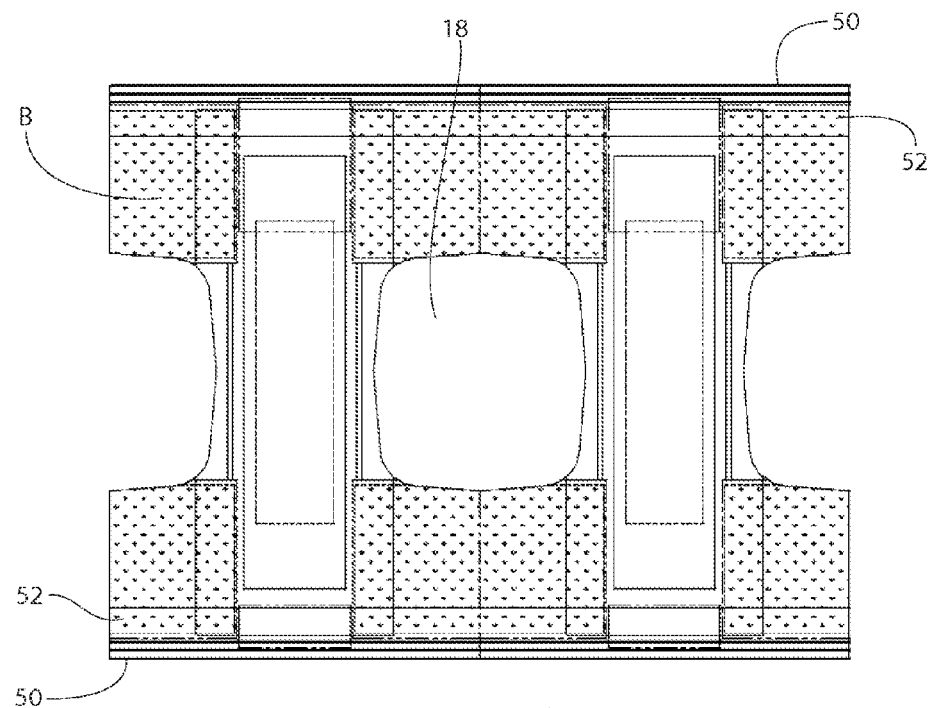
Figure 16:
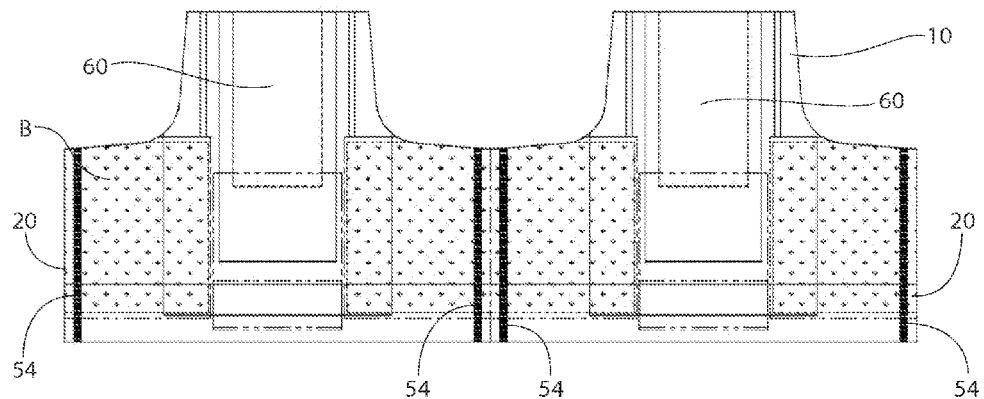

Referring now to FIG. 15, a leg opening portion 18 of the web 10 is then die-cut and removed, preferably by vacuum. As shown in FIG. 16, the web 10 is folded over longitudinally and side seam bonds 54 are formed, again preferably but not necessarily ultrasonically, in the regions shown, in order to join the front and the rear of the disposable product together to form a pant style product.

Figure 17:
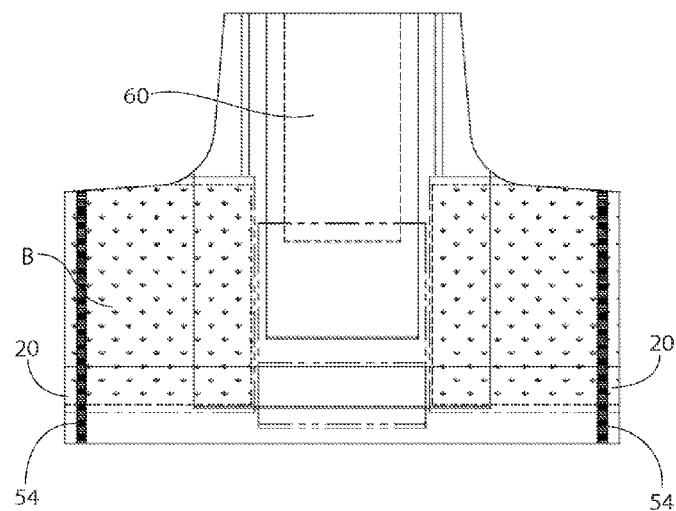

As shown in FIG. 17, discrete products are formed by severing in between successive side seam bonds 54, and these products can then be stacked and packaged as desired.

Figure 18:
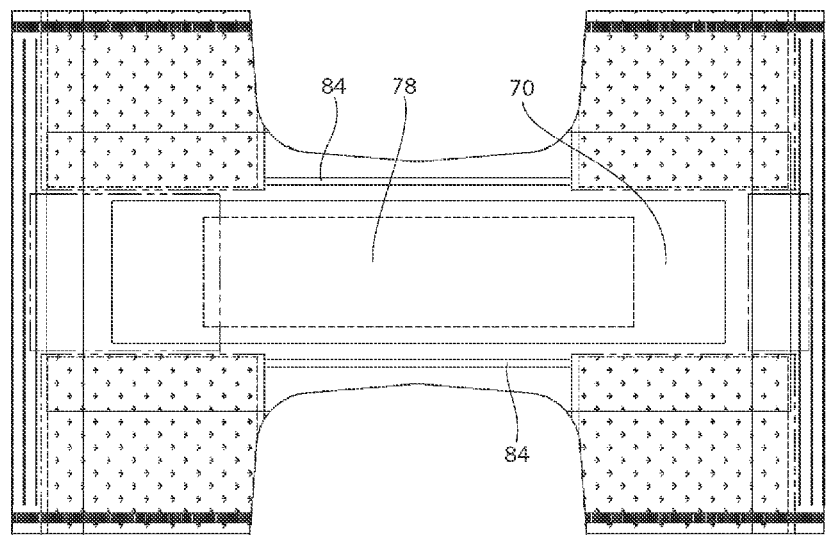
FIG. 18 is a laid open product formed according to methods of the present invention.

Referring to FIGS. 18 and 19, a product produced by the methods of the present invention is shown first laid open (FIG. 18) and in cross-section (FIG. 19).

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method of forming a disposable product comprising:
   forming an absorbent core;
   capturing the absorbent core between a topsheet and a backsheet to form a core insert;
   supplying a chassis web;
   coupling a character strip to said chassis web;
   coupling a stretch material to said chassis web over said character strip;
   coupling an intermittent side panel material to said chassis web over said stretch material;
   bonding said side panel to said chassis web;
   removing a portion of said stretch film from said chassis web;
   coupling said core insert with said chassis web.

2. A method according to claim 1, wherein said topsheet assembly is a three-ply laminate comprising an acquisition layer, a non-woven layer, and a cuff assembly.

3. A method according to claim 1, the method further comprising:
   providing waist elastic at a waist cap portion of said chassis web;
   folding said waist cap portion of said chassis web over itself and coupling said portion with said chassis web to form a waist elastic portion of said chassis web.

4. A method according to claim 1, the method further comprising:
   removing a leg portion from said chassis web;
   folding said product and bonding said folded product at side seam locations.

* * * * *